(12) United States Patent
McIntyre

(10) Patent No.: US 8,153,695 B2
(45) Date of Patent: Apr. 10, 2012

(54) METHODS FOR INHIBITING POST-SURGICAL ADHESIONS

(75) Inventor: Jon T. McIntyre, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 520 days.

(21) Appl. No.: 12/128,671

(22) Filed: May 29, 2008

(65) Prior Publication Data

US 2008/0300319 A1 Dec. 4, 2008

Related U.S. Application Data

(60) Provisional application No. 60/933,036, filed on Jun. 4, 2007.

(51) Int. Cl.
*A61K 31/015* (2006.01)
(52) U.S. Cl. ...................................................... 514/763
(58) Field of Classification Search .................... 514/763
See application file for complete search history.

(56) References Cited

U.S. PATENT DOCUMENTS

| | | | |
|---|---|---|---|
| 4,917,826 A | | 4/1990 | Johnson et al. |
| 5,795,584 A | * | 8/1998 | Totakura et al. ............... 424/426 |
| 5,895,412 A | | 4/1999 | Tucker |
| 6,235,796 B1 | | 5/2001 | Niazi |
| 6,461,640 B1 | | 10/2002 | Hubbell et al. |
| 7,073,512 B2 | | 7/2006 | Koninckx |
| 2005/0208095 A1 | | 9/2005 | Hunter et al. |
| 2005/0256160 A1 | | 11/2005 | Habashita et al. |
| 2005/0271727 A1 | | 12/2005 | Yao |

OTHER PUBLICATIONS

Ozgun et al. (Journal of Surgical Research, vol. 103, pp. 141-145; 2002).*
Binnebosel et al. (Langenbecks Arch Surg, vol. 393, pp. 59-66; 2008).*
Miyako et al. (International Journal of Pharmaceutics, vol. 393, pp. 48-54; 2010).*
L. Mettler et al., "Prospective Clinical Trial of SprayGel as a Barrier to Adhesion Formation: An Interim Analysis", The Journal of the American Association of Gynecologic Laparoscopists, Aug. 2003, vol. 10, No. 3, pp. 339-344.
S. Rimbach, "The development of a German Consensus on adhesion management", Adhesions News & Views, Issue 8, Nov. 2005, pp. 26-29.
J.S. Chickos et al., "Enthalpies of Sublimation of Organic and Organometallic Compounds. 1910-2001," J. Phys. Chem. Ref. Data, 31(2), 2002, pp. 537, 595 and 605.
I. Brückle et al., "Cyclododecane: technical note on some uses in paper and objects conservation," JAIC 1999, 38 (2), Article 4, pp. 162-175.
E. Jaegers, "Cyclododecane," Cons DistList, Feb. 14, 1999, downloaded on Oct. 18, 2006 from http://palimpsest.stanford.edu/byform/mailing-lists/cdl/1999/0218.html.
"Cyclododecane (CCD)", Downloaded on Oct. 19, 2006 from http://www.cyclododecane.net/html_e/cyclododecan.htm.
"Camphene, Technically Pure", Downloaded on Oct. 19, 2006 from http://www.cyclododecane.net/html_e/camphen.htm.
J.P. Elder, "Sublimation measurements of pharmaceutical compounds by isothermal thermogravimetry," Journal of Thermal Analysis, vol. 49, 1997, pp. 897-905.

\* cited by examiner

*Primary Examiner* — Jeffrey S. Lundgren
*Assistant Examiner* — Nelson Blakely, III
(74) *Attorney, Agent, or Firm* — Mayer & Williams PC; David B. Bonham; Keum J. Park

(57) ABSTRACT

In accordance with one aspect of the invention, a method is provided in which post-surgical adhesions at a surgical site in a patient are inhibited. The method includes topically applying a liquid composition comprising a hydrophobic species, which has a melting point above normal body temperature, to tissue at the surgical site in an amount effective to inhibit the formation of adhesions during healing.

16 Claims, 1 Drawing Sheet

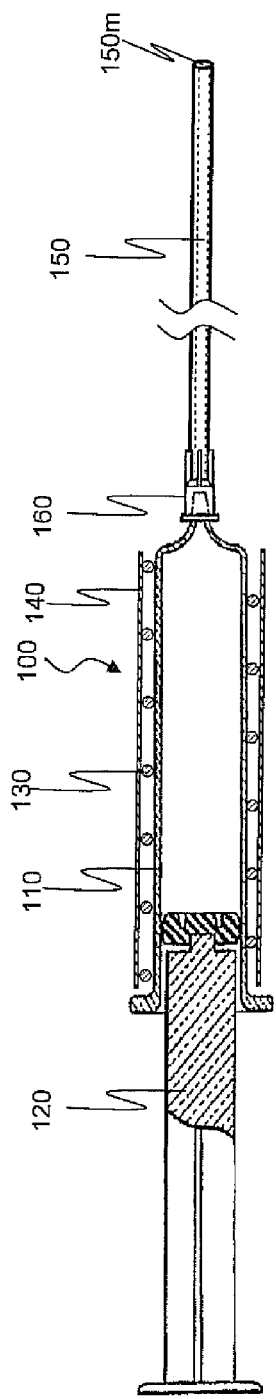
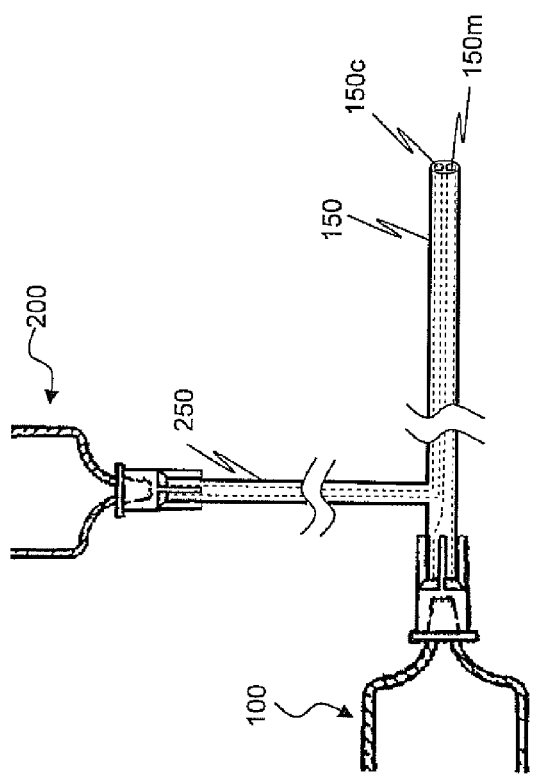

METHODS FOR INHIBITING POST-SURGICAL ADHESIONS

STATEMENT OF RELATED APPLICATION

This application claims the benefit of U.S. Provisional Patent Application Ser. No. 60/933,036, filed Jun. 4, 2007, entitled "Methods for Preventing or Inhibiting Post-Surgical Adhesions", which is incorporated by reference herein in its entirety.

FIELD OF THE INVENTION

The present invention is directed to methods for preventing or inhibiting post-surgical adhesions in a patient.

BACKGROUND OF THE INVENTION

Surgical adhesions are abnormal scar tissue that can form inside the body as a result of the healing process that follows open or minimally invasive surgical procedures, including abdominal, gynecologic, cardiothoracic, spinal, plastic, vascular, ENT, ophthalmologic, urological, neurological, orthopedic surgery, among others. Briefly, localized areas of injury trigger inflammatory and healing responses that result in healing and scar tissue formation. If scarring results in the formation of fibrous tissue bands or adherence of adjacent anatomical structures that are normally separate, surgical adhesion formation is said to have occurred. Complications from surgical adhesions are a major cause of failed surgical therapy and are a leading cause of bowel obstruction and infertility. Other adhesion-related complications include chronic back or pelvic pain, urethral obstruction and voiding dysfunction. Relieving the post-surgical complications caused by adhesions generally requires another surgery. However, the second surgery is further complicated by adhesions that formed as a result of the previous surgery. In addition, the second surgery can result in further adhesions and a continuing cycle of additional surgical complications. Although a potential complication of any surgical intervention, surgical adhesions are particularly problematic in GI surgery (causing bowel obstruction), gynecological surgery (causing pain and/or infertility), tendon repairs (causing shortening and flexion deformities), joint capsule procedures (causing capsular contractures), and nerve and muscle repair procedures (causing diminished or lost function).

Without wishing to be bound by theory, it is believed that adhesions generally begin to form within the first several days after surgery. Adhesion formation is typically an inflammatory reaction in which various factors are released, increasing vascular permeability and resulting in fibrinogen influx and fibrin deposition. This deposition forms a matrix that can bridge abutting tissues. Fibroblasts accumulate, attach to the matrix, deposit collagen and induce angiogenesis. If this cascade of events can be prevented within the first few days following surgery, then adhesion formation may be inhibited.

Various modes of adhesion prevention have been examined, including (1) reduction of local tissue inflammation, (2) prevention of fibrin deposition and (3) removal of fibrin deposits. For example, inflammation may be reduced by the administration of drugs such as corticosteroids and non-steroidal anti-inflammatory drugs. The removal of fibrin deposits has been investigated using proteolytic and fibrinolytic enzymes.

Fibrin deposition may be prevented through the use of physical barriers, which have the advantage of physically preventing adjacent tissues from contacting each other and thereby reducing the probability that they will scar together. Examples of barrier materials include films such as those formed from oxidized regenerated cellulose (e.g., Interceed™, Gynecare, Ethicon division of Johnson and Johnson, Arlington, Tex., USA), hyaluronate/carboxymethylcellulose (Seprafilm™, Genzyme Corporation, Cambridge, Mass.) and polytetrafluoroethylene (Preclude™, W.L. Gore & Associates, Flagstaff, Ariz., USA), among others.

There are also a number of sprays, solutions, gels, and powers that are intended for use as adhesion barriers including those formed from hyaluronic acid (Sepracoat™, Genzyme Corporation), crosslinked hyaluonan (Sepragel™, Genzyme Corporation), and cross-linked ferric hyaluronate (Intergel™, Gynecare), Ringers lactated solution, a solution of dextran 70 in dextrose (Hyskon™, Cooper Surgical Shelton, Conn., USA), icodextrin solution (Adept™, Innovata plc, Farnham, Surrey, United Kingdom), polyglycan ester in a gelatin matrix (Adcon™, Gliatech Inc., Cleveland, Ohio, USA), sprayable functionalized polyethylene glycol (SprayGel™, Confluent Surgical Inc. Waltham, Mass., USA), a gel composed of polyethylene oxide and carboxymethylcellulose stabilized by calcium chloride (Oxiplex™, FzioMed, Inc., San Luis Obispo, Calif., USA), a synthetic surfactant formulation of dipalmitoylphosphatidycholine and phosphatidyl glycerol (Adsurf™ from Britannia Pharmaceuticals Ltd., United Kingdom), and a sprayable self-polymerizing liquid hydrogel (Adhibit™, Cohesion Technologies, Palo Alto, Calif., USA), among others.

Further information regarding adhesion barrier materials can be found, for example, in S. Rimbach, *Adhiesions News $ Views*, Issue 8, November 2005, pp. 26-29, U.S. 2005/0208095 to Hunter et al., and U.S. Pat. No. 6,235,796 to Niazi.

SUMMARY OF THE INVENTION

In accordance with one aspect of the invention, a method is provided for preventing or inhibiting post-surgical adhesions at a surgical site in a patient. The method comprises topically applying a liquid composition comprising a hydrophobic species, which has a melting point above normal body temperature, to tissue at the surgical site in an amount effective to prevent or inhibit the formation of adhesions during healing. Application of the liquid composition results in the formation of a solid adhesion barrier layer on the tissue. Moreover, the properties of the hydrophobic species are such that the adhesion barrier sublimes in vivo after the surgical site is closed.

Further enumerated aspects of the invention follow:

Aspect 1. A method of preventing or inhibiting post-surgical adhesions at a surgical site in a patient comprising topically applying a liquid composition, which comprises a hydrophobic species having a melting point above normal body temperature, to tissue at the surgical site in an amount effective to prevent or inhibit the formation of adhesions during healing, wherein application of said liquid composition results in the formation of a solid barrier layer on said tissue, and wherein said solid barrier layer sublimes in vivo after the surgical site is closed.

Aspect 2. The method of Aspect 1, wherein said melting point is between 40° C. and 70° C.

Aspect 3. The method of Aspect 1, wherein said hydrophobic species has a vapor pressure at 20° C. of at least 1 Pa.

Aspect 4. The method of Aspect 1, wherein said hydrophobic species has an enthalpy of sublimation at 298K of at most 100 kJ/mol.

Aspect 5. The method of Aspect 1, wherein a solid layer formed from said hydrophobic species sublimates ex vivo in air at room temperature at a rate of at least 0.05 mm/day.

Aspect 6. The method of Aspect 1, wherein said hydrophobic species is a hydrocarbon.

Aspect 7. The method of Aspect 1, wherein said hydrophobic species is a cyclic hydrocarbon.

Aspect 8. The method of Aspect 1, wherein said hydrophobic species is camphene.

Aspect 9. The method of Aspect 1, wherein said hydrophobic species cyclododecane.

Aspect 10. The method of Aspect 1, wherein said liquid composition is a melt.

Aspect 11. The method of Aspect 10, wherein said melt is applied to said tissue at a temperature that is sufficiently high to necrose said tissue.

Aspect 12. The method of Aspect 10, wherein a cooling fluid is administered to assist with the cooling of the melt.

Aspect 13. The method of Aspect 1, wherein said liquid composition is a solution that comprises a solvent and said hydrophobic species.

Aspect 14. The method of Aspect 13, wherein said solvent has boiling point above normal body temperature.

Aspect 15. The method of Aspect 13, wherein said solvent has a boiling point that is below room temperature.

Aspect 16. The method of Aspect 15, wherein said solvent further acts as a propellant in a spraying process.

Aspect 17. The method of Aspect 15, wherein said solvent comprises methane and butane.

Aspect 18. The method of Aspect 1, wherein said surgical site is within the peritoneal cavity.

Aspect 19. A medical device that comprises first and second lumens, wherein the medical device is configured to deliver a first fluid medium through the first lumen at a temperature above normal body temperature and to concurrently or sequentially deliver a second fluid medium through the second lumen at a temperature below normal body temperature.

Aspect 20. The medical device of Aspect 19, wherein the first lumen is heated.

Further aspects and embodiments, as well as various advantages of the invention will become clear upon reviewing the Detailed Description to follow.

BRIEF DESCRIPTION OF THE DRAWINGS

FIG. 1 is a schematic, partial cross-sectional view of a syringe-fed laparoscopic catheter in accordance with an embodiment of the invention.

FIG. 2 is a schematic, partial cross-sectional view of a syringe-fed laparoscopic catheter in accordance with another embodiment of the invention.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention.

As noted above, in accordance with one aspect of the invention, a method is provided in which post-surgical adhesions at a surgical site in a patient are prevented or inhibited. The method comprises topically applying a liquid composition comprising a hydrophobic species, which has a melting point above normal body temperature, to tissue at the surgical site in an amount effective to prevent or inhibit the formation of adhesions during healing. Application of the liquid composition results in the formation of a solid barrier layer on the tissue. Moreover, the properties of the hydrophobic species are such that the adhesion barrier sublimes in vivo after the surgical site is closed.

"Patients" include vertebrate subjects, particularly humans and various other mammals including pets and livestock.

In some embodiments, the hydrophobic species is selected such that a film formed therefrom sublimates at a rate of at least 0.005 mm/day in air at room temperature (25° C.). Hydrophobic species meeting this criterion include various hydrocarbons (i.e., non-polymeric molecules formed from hydrogen and carbon atoms), specific examples of which include cyclic hydrocarbons such as cyclododecane,

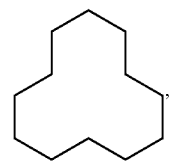

camphene,

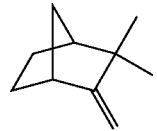

and combinations of the same. The reported sublimation rate of cyclododecane is about 0.03-0.04 mm/day and the reported sublimation rate for camphene is about 0.4 mm/day. I. Brukle et al., "Cyclododecane: technical note on some uses in paper and objects conservation," JAIC 1999, 38(2), Article 4, 162-175 and E. Jaegers, "Cyclohexane," Cons DistList, Feb. 14, 1999, http://palimpsest.stanford.edu/byform/mailing-lists/cdl/1999/0218.html.

For a given material, sublimation rate is related to the enthalpy of sublimation. In particular, the sublimation enthalpy of a given compound can be calculated by measuring sublimation rates at set isothermal temperatures and fitting these data to the Arrhenius equation, among other methods. J. P. Elder, "Sublimation measurements of pharmaceutical compounds by isothermal thermogravimetry," Journal of Thermal Analysis and Calorimetry, 44(2), June 1997, 897-905. Hydrophobic species which readily sublimate, including cyclododecane and camphene, among others, typically have low enthalpies of sublimation. In this regard, in certain embodiments, the hydrophobic species that is selected has an enthalpy of sublimation at 298K of 250 kJ/mol or less, for example, from 250 kJ/mol to 100 kJ/mol to 50 kJ/mol to 25 kJ/mol or less. As specific examples, cyclododecane has a reported enthalpy of sublimation at 298K of ~76 kJ/mol whereas camphene has a reported enthalpy of sublimation of ~47 kJ/mol. J. S. Chickos et al., "Enthalpies of Sublimation of Organic and Organometallic Compounds. 1910-2001," J. Phys. Chem. Ref. Data, 31(2), 2002, 537-698.

Another characteristic of compounds that readily sublimate is that they have high vapor pressures relative to other solids. In this regard, in certain embodiments, the hydrophobic species that is selected has a vapor pressure at 20° C. of at least 1 Pa, for example ranging from 1 Pa to 2 Pa to 5 Pa to 10

Pa to 50 Pa to 100 Pa to 100 Pa or more. For instance, cyclododecane has a reported vapor pressure at 20° C. of ~0.1 hPa (10 Pa), whereas camphene has a reported vapor pressure at 20° C. of ~3.3 mbar (330 Pa). Data from Hans-Michael Hangleiter, GmbH, Otzberg, Germany.

As previously noted, in the method of the present invention, a liquid composition comprising one or more hydrophobic species, which has/have a melting point above normal body temperature, is topically applied to tissue at a surgical site in an amount effective to prevent or inhibit the formation of adhesions during healing. Application of the liquid composition results in the formation of a solid adhesion barrier layer on the tissue. Liquid compositions meeting these criteria include melts and solutions.

Where a melt is applied, the hydrophobic species that is selected typically has a melting point ranging from 40° C. to 50° C. to 60° C. to 70° C. Cyclododecane has a reported melting point of 58-61° C. and camphene has a reported melting point of 45-46° C.

Such a material can applied using a suitable device, for example, a catheter, which may have an optional spray head to disperse the melt at the time of application. For instance, referring to FIG. 1, a syringe 100 is shown, which has a barrel 110 and a plunger 120. A hydrocarbon species may be heated to above its melting point in the syringe 100, for example, via a small heater surrounding the syringe barrel (e.g., one comprising a heating coil 130 covered by a sheath 140 is shown). The hydrocarbon species melt may be delivered to the surgical site from the syringe barrel 110 by advancing the plunger 120, which forces the melt through the channel of a catheter, in this instance, a laparoscopic catheter in the form of a long nozzle 150, which is attached to the syringe barrel 110 by a suitable fitting 160. The interior of the syringe barrel 110 is in fluid communication with the lumen 150m of the nozzle 150. The nozzle 150 also may be optionally supplied with a heating element (not shown) to ensure that the hydrocarbon species is maintained in a melt state.

The nozzle may also be optionally supplied with a second channel for the application of a cooling fluid, if desired. For example, FIG. 2 is an illustration of a device similar to that of FIG. 1 in that it contains a heated syringe 100 and a nozzle 150 having a lumen 150m through which the hydrocarbon species melt can be delivered. In addition, the nozzle 150 is provided with a lumen 150c through which a fluid coolant (e.g., a liquid or a gas) can be delivered, for example, from a syringe 200 through tubing 250 in the embodiment shown. Thus, in some embodiments, the invention comprises a medical device that comprises first and second lumens, wherein the medical device is configured to deliver a first fluid medium through the first lumen at a temperature above normal body temperature and to concurrently (or sequentially) deliver a second fluid medium through the second lumen at a temperature below normal body temperature.

In a specific example, cyclododecane may be applied in a melted state to a surgical site during a laparoscopic procedure (e.g., a procedure involving fulguration of endometriosis lesions, myomectomy, abdominal hysterectomy, ovarian surgery, etc.). A waxy solid film will form as the molten cyclododecane cools on the tissue, without appreciable tissue penetration (i.e., because the cyclododecane is hydrophobic). The cyclododecane film will act as a barrier between two opposing tissue layers during the initial healing stages after surgery. The formation of a solid film may be accelerated by the immediate application of a cooling fluid such as a stream of air or a aqueous liquid through an optional channel in the application device (e.g., as above) or via a separate device. This may, for example, to prevent unwanted tissue damage, although this may be unnecessary in many cases as the surgical area will already have undergone tissue dam age, incisional or otherwise.

In some embodiments, the cyclododecane may be heated to well above its melting temperature and applied to untreated lesions (e.g., endometriosis, etc.), allowing the heat from the melted cyclododecane to ablate (necrose) the lesions. Subsequently, as the material cools, it forms an adhesion barrier over the treated area. Cooling may be used to confine the heat treated zone to the tissue covered by the barrier.

In other embodiments of the invention, one or more hydrophobic species is/are dissolved in a non-polar solvent and applied to tissue.

For example, the solvent may have a boiling point above normal body temperature in some instances. Examples of solvents which have been reported to be good solvents for cyclododecane include pentane (b.p. 36° C.) and isooctane (p.b. 99° C.). Solutions of cyclododecane in organic solvents have been reported to result in layers that are thinner and more porous than their melt-based counterparts. Hans-Michael Hangleiter, GmbH, Otzberg, Germany.

In some instances, the solvent has a boiling point below body temperature, more preferably, below room temperature. In this regard, a liquid composition of cyclododecane is available commercially from Hans-Michael Hangleiter, GmbH (Otzberg, Germany) for delivery as a spray, in which low-boiling point solvents (i.e., methane and butane) find use both as a non-polar solvent system for the cyclododecane and as a propellant for the composition.

Regardless of the method by which the hydrophobic species is/are applied at the surgical site, the resulting film will ultimately disappear due to sublimation over a period of days or weeks (e.g., over a period of 0.5 week or less to 1 week to 2 weeks to 4 weeks to 8 weeks or more), with the actual time depending on the hydrocarbon species and the thickness of the film formed therefrom, among other factors. For example, at a sublimation rate of 0.04 mm/day, a 0.4 mm thick barrier of cyclododecane will disappear over a period of about 10 days in air. The sublimation of such a film in vivo may be delayed, compared to its rate in air, due to the enclosed nature of a given surgical site (e.g., the peritoneal cavity) after surgery, although this may be at least somewhat offset by the elevated temperatures in vivo.

The invention claimed is:

1. A method of inhibiting post-surgical adhesions at a surgical site in a patient comprising topically applying a liquid composition, which comprises a hydrophobic species having a melting point above normal body temperature, to tissue at the surgical site in an amount effective to inhibit the formation of adhesions during healing, wherein application of said liquid composition results in the formation of a solid barrier layer on said tissue, wherein said solid barrier layer sublimes in vivo after the surgical site is closed, and wherein said hydrophobic species is a cyclic hydrocarbon.

2. The method of claim 1, wherein said melting point is between 40° C. and 70° C.

3. The method of claim 1, wherein said hydrophobic species has a vapor pressure at 20° C. of at least 1 Pa.

4. The method of claim 1, wherein said hydrophobic species has an enthalpy of sublimation at 298K of at most 100 kJ/mol.

5. The method of claim 1, wherein the solid layer formed from said hydrophobic species sublimates ex vivo in air at room temperature at a rate of at least 0.05 mm/day.

6. The method of claim 1, wherein said hydrophobic species is camphene.

7. The method of claim 1, wherein said liquid composition is a melt.

8. The method of claim 7, wherein said melt is applied to said tissue at a temperature that is sufficiently high to necrose said tissue.

9. The method of claim 7, wherein a cooling fluid is administered to assist with the cooling of the melt.

10. The method of claim 1, wherein said liquid composition is a solution that comprises a solvent and said hydrophobic species.

11. The method of claim 10, wherein said solvent has boiling point above normal body temperature.

12. The method of claim 10, wherein said solvent has a boiling point that is below room temperature.

13. The method of claim 12, wherein said solvent further acts as a propellant in a spraying process.

14. The method of claim 12, wherein said solvent comprises methane and butane.

15. The method of claim 1, wherein said surgical site is within the peritoneal cavity.

16. A method of inhibiting post-surgical adhesions at a surgical site in a patient comprising topically applying a liquid composition, which comprises cyclododecane, to tissue at the surgical site in an amount effective or inhibit the formation of adhesions during healing, wherein application of said liquid composition results in the formation of a solid barrier layer on said tissue, and wherein said solid barrier layer sublimes in vivo after the surgical site is closed.

* * * * *